US007090875B2

(12) United States Patent
Miyazaki et al.

(10) Patent No.: US 7,090,875 B2
(45) Date of Patent: Aug. 15, 2006

(54) EXTERNAL SKIN PREPARATIONS AND PROCESS FOR PRODUCING THE SAME

(75) Inventors: Kouji Miyazaki, Tokyo (JP); Satoshi Yoshikawa, Tokyo (JP); Ryoko Iizuka, Tokyo (JP); Takashi Kinoshita, Tokyo (JP); Naohito Saito, Tokyo (JP); Katsuyoshi Chiba, Tokyo (JP); Naomi Kondo, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 15 days.

(21) Appl. No.: 10/450,453

(22) PCT Filed: Dec. 6, 2001

(86) PCT No.: PCT/JP01/10698

§ 371 (c)(1),
(2), (4) Date: Jun. 19, 2003

(87) PCT Pub. No.: WO02/49656

PCT Pub. Date: Jun. 27, 2002

(65) Prior Publication Data

US 2004/0029829 A1    Feb. 12, 2004

(30) Foreign Application Priority Data

Dec. 19, 2000  (JP) .............................. 2000-385794
Dec. 27, 2000  (JP) .............................. 2000-398891

(51) Int. Cl.
*A61K 36/00* (2006.01)
(52) U.S. Cl. ...................... 424/757; 424/115; 424/93.4; 435/252.1; 514/725
(58) Field of Classification Search ................ 424/757, 424/687, 115, 93.45
See application file for complete search history.

(56) References Cited

U.S. PATENT DOCUMENTS

| 3,937,843 | A | * | 2/1976 | Osaka et al. | |
| 3,991,480 | A | * | 11/1976 | Menge | |
| 5,705,205 | A | * | 1/1998 | Brunerie | ...................... 426/44 |
| 6,338,855 | B1 | | 1/2002 | Albacarys et al. | .......... 424/409 |
| 6,461,627 | B1 | * | 10/2002 | Ichioka et al. | |
| 6,599,543 | B1 | * | 7/2003 | Yokoyama et al. | |

FOREIGN PATENT DOCUMENTS

| CN | 1166960 A | * | 12/1997 |
| FR | 2 784 029 | | 4/2000 |
| JP | 55-64754 | | 5/1980 |
| JP | 57-094264 | | 6/1982 |
| JP | 58043757 | * | 3/1983 |
| JP | 60-75264 | | 4/1985 |
| JP | 60-199349 | | 10/1985 |
| JP | 62-036304 | | 2/1987 |
| JP | 01-102011 | | 4/1989 |
| JP | 03216163 A | * | 1/1991 |
| JP | 3-126163 | | 5/1991 |
| JP | 03-127713 | | 5/1991 |
| JP | 06-279227 | | 10/1994 |
| JP | 8-104647 | | 4/1996 |
| JP | 08-301748 | | 11/1996 |
| JP | 08-310934 | | 11/1996 |
| JP | 09-100211 | | 4/1997 |
| JP | 9-183733 | | 7/1997 |
| JP | 10-175815 | | 6/1998 |
| JP | 10-287540 | | 10/1998 |
| JP | 2000-72616 | | 3/2000 |
| WO | 00/21501 | | 4/2000 |

OTHER PUBLICATIONS

English abstract of WO 00/21501 (Apr. 2000).*
Kouji Miyazaki et al.: "Dermatological researches of isoflavone and bifidobacterium-fermented soya milk extract" vol. 28, No. 12, pp. 112-117—Fragrance Journal 2000.
Philip S. Tong et al.: "Trans retinoic acid enhances the growth response of epidermal keratinocytes to epidermal growth factor and transforming growth factor beta" The Journal of Investigative Dermatology, vol. 94, No. 1, pp. 126-131, 1990.
James Varani et al.: "Molecular mechanisms of intrinsic skin aging and retinoid-induced repair and reversal" The Journal of Investigative Dermatology, pp. 57-60, 1998.
Raija Tammi et al.: "Hyaluronate accumulation in human epidermis treated with retinoic acid in skin organ culture" The Journal of Investigative Dermatology, vol. 92, No. 3, pp. 326-332, 1989.
Reinhard Wanner et al.: "The loss of demosomes after retinoic acid treatment results in an apparent inhibition of HaCat keratonocyte differentiation" Arch Dermatol Res, vol. 291, pp. 346-353, 1999.
Constantin E. Orfanos et al.: "Retinoic acid in psoriasis: its value for topical therapy with and without corticosteroids" British Journal of Dermatology, vol. 88, pp. 167-181, 1973.
Dan K. Chalker et al.: "Efficacy of topical isotretinoin 0.05% gel in acne vulgaris: results of a multicenter, double-blind investigation" Journal of the American Academy of Dermatology, vol. 17, pp. 251-254, 1987.
Jonathan S. Weiss et al.: "Topical tretinoin improves photoaged skin" JAMA, vol. 259, No. 4, pp. 527-532, 1988.

(Continued)

*Primary Examiner*—Susan D. Coe
(74) *Attorney, Agent, or Firm*—Oblon, Spivak, McClelland, Maier & Neustadt, P.C.

(57) ABSTRACT

External skin preparations containing one or more members selected from among a fermentation product, which is obtained by treating a bean extract with a microorganism, vitamin A and its derivatives. By potentiating skin cells and accelerating the production of hyaluronic acid, these preparations exert effects of preventing and relieving skin roughness, improving keratin, moistening, and preventing and relieving skin tension failure and wrinkles, thereby efficaciously retarding skin aging.

19 Claims, 8 Drawing Sheets

OTHER PUBLICATIONS

Takayoshi Tadaki et al.: "The effect of topical tretinoin on the photodamaged skin of the Japanese" Tohoku J. Exp. Med., vol. 169, pp. 131-139, 1993.

Kouji Miyazaki et al.: "Dermatological researches of isoflavone and bifidobacterium-fermented soya milk extract" vol. 28, No. 12, pp. 112-117 2000.

* cited by examiner

Mean value ± standard error (N=6)
a) indicates a significant increase over the control (p<0.01), and over SB and RA (p<0.05).

EXTERNAL SKIN PREPARATIONS AND PROCESS FOR PRODUCING THE SAME

FIELD OF THE INVENTION

The present invention relates to a skin preparation for external application and, more particularly, to a skin preparation for external application exhibiting an effect of preventing and relieving skin roughness, thereby retarding skin aging. The present invention also relates to a process for producing the skin preparation.

DESCRIPTION OF BACKGROUND ART

Due to a low turnover rate of the horny cell layer and a decrease in the hyaluronic acid content, the aged skin is known to dry easily, to become easily roughened, dried, wrinkled, or loosened, and to decrease in thickness, resulting in impaired elasticity. In addition to aging, the above phenomena are considered to be caused by external factors such as exposure to ultraviolet rays, drying, and oxidation which cause a decrease in the function of epidermic cells and dermal fibroblasts, and decomposition of hyaluronic acid.

Cosmetics containing raw materials extracted from naturally occurring materials such as galenicals and chemically synthesized raw materials have been used to improve such aged skin. These cosmetics have been known to provide the skin with moisture and flexibility due to a moisturizing effect and a physicochemical effect of film formation and the like (Japanese Patent Applications Laid-open No. 6-279227 and No. 8-310934). Although the cosmetics are effective in improving a dry skin surface, the effect is temporary and the improvement is not essential.

For this reason, an effort of increasing hyaluronic acid production by promoting the metabolism function of the skin has been undertaken. Retinoic acid, for example, which is a metabolite of vitamin A and one of the bioactive isomers of vitamin A, is known to exhibit a variety of effects on the physiological activity of skin, such as an effect of promoting the growth of epidermic cells and fibroblasts (Tong P S et al., J. Invest. Dermatol. 94, 126–131, 1990, Varani J et al., J. Investig. Dermatol. Symp. Proc. 3, 57–60,1998), an effect of promoting hyaluronic acid production (Tammi R et al., J. Invest. Dermatol. 92, 326–332, 1989), a cornification improving effect (Wanner R et al., Arch. Dermatol. Res. 291, 346–353, 1999), an anti-psoriasis effect (Orfanos C E et al., Br. J. Dermatol. 88, 167–182, 1973), an anti-acne effect (Chalker D K et al., J. Am. Acad. Dermatol. 17, 251–254, 1987), an anti-wrinkle effect (Weiss J S et al., JAMA 259, 527–535, 1988, Tadaki T et al., Tohoku J. Exp. Med. 169, 131–139, 1993), and a photo-aged skin improving effect (Kligman A M et al., J. Am. Acad. Dermatol. 15, 836–859, 1986). Retinoic acid preparations have already been used as a photo-aged skin improver and a wrinkle improver in the US.

However, because retinoic acid is strongly irritating, the use of retinol, which is less irritating and less physiologically active, has been investigated. The use of retinol combined with various compounds to increase its physiological activity has also been investigated. A combined use of retinol with fatty acid amide (Japanese Patent Application Laid-open No. 08-301748) or dimethylimidazoline (Japanese Patent Application Laid-open No. 9-100211) is known to provide a synergistic effect on epidermic cell activation.

However, the conventional preparations containing vitamin A such as retinol, retinoic acid, or their derivatives cannot necessarily bring about a sufficient effect of activating epidermic cells or increasing hyaluronic acid production.

On the other hand, cosmetic compositions containing a bean extract such as soybean milk have been known and reported as having a moisture retention effect and a detergent effect (Japanese Patent Application Laid-open No. 62-36304 etc.). In addition, the use of fermented bean products in cosmetic compositions and the like, for example, products obtained by fermenting soybean milk with microorganisms of genus *Rhizopus* (Japanese Patent Application Laid-open No. 1-102011), genus *Lactobacillus* (Japanese Patent Application Laid-open No. 3-127713), or genus *Bifidobacterium* (Japanese Patent Application Laid-open No. 10-287540) have been known.

However, the effect of fermented bean products on epidermic cell activation and promotion of hyaluronic acid production when combined with other components has not been known at all.

The cosmetic compositions and the like containing fermented bean products may have a soybean odor, fermented odor, or irritating odor. The odor may be associated with a negative image of a rotted product and impart the user an unpleasant feeling. However, no effective method of decreasing the odor of fermented soybean products has been known.

An object of the present invention is to provide a skin preparation for external application exhibiting an effect of preventing and relieving skin roughness, a cornification improving effect, a moisturizing effect, and an effect of preventing and improving wrinkled or loosened skin by activating dermal cells and promoting production of hyaluronic acid, and therefore effective for retarding skin aging. The present invention also provides a process for producing the skin preparation.

DISCLOSURE OF THE INVENTION

In view of the above situation, the inventors of the present invention have conducted extensive studies on the effect of activating epidermic cells or increasing hyaluronic acid production possessed by vitamin A and derivatives thereof. As a result, the inventors have found that if vitamin A and the derivatives thereof are combined with a fermented product obtained by reacting microorganisms with a bean extract, not only the cell activation effect of vitamin A and the derivatives thereof can be promoted, but also production of hyaluronic acid in the skin tissue can be remarkably promoted. The inventors have further found that a skin preparation obtained by combining these components can improve dry, roughened, wrinkled, or loosened skin and prevent the skin from aging. The inventors have further found that a skin preparation for external application having a favorable taste imparting a decreased odor originating from the fermented product such as a soybean odor or a fermented or irritating odor can be obtained by using a deodorized fermented product which can be produced by a process comprising an additional step of causing the fermented product to contact with one or more members selected from the group consisting of a carbonate and talc.

Specifically, the present invention provides a skin preparation for external application comprising a fermented product obtained by causing a microorganism to react with a bean extract and vitamin A and/or a derivative thereof.

The present invention further provides the above skin preparation for external application, wherein the fermented product is a deodorized fermented product obtained by a process comprising the following steps (a) and (b):

(a) a step of causing one or more kinds of microorganisms to react with a bean extract and (b) a step of causing the fermented product obtained in the step (a) to contact with one or more members selected from the group consisting of a carbonate and talc.

The present invention further provides the skin preparation for external application defined above, wherein the following step (c) is added after the step (a):

(c) a step of adjusting the pH with an organic acid.

The present invention further provides the skin preparation for external application defined above, wherein the following step (d) is added after the step (b):

(d) a step of leaving the product while stirring at a teperature of 20° C. or less, and preferably at 5° C. or less.

Specifically, the present invention provides a process of the skin preparation for external application comprising the following steps (e) and (f):

(e) a step of causing one or more kinds of microorganisms to react with a bean extract and (f) a step of causing the fermented product obtained in (e) to contact with one or more members selected from the group consisting of a carbonate and talc.

DETAILED DESCRIPTION OF THE INVENTION AND PREFERRED EMBODIMENT

Figure 1:
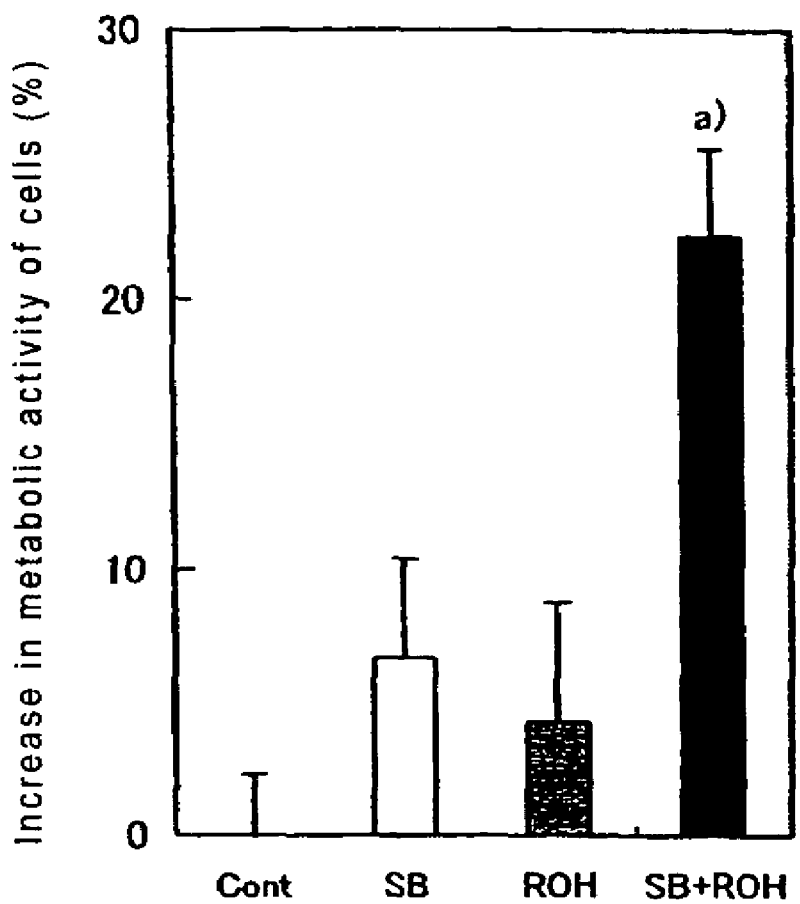
FIG. 1 shows the effect of the combined use of a fermented product 1 (SB) and all-trans-retinol (ROH) on the metabolism activity of incubated human epidermic cells.

The fermented product obtained by causing a microorganism to react with a bean extract (hereinafter referred to simply as "fermented product") is generally called fermented soybean milk and is used as a raw material for foods.

There are no specific limitations to the microorganisms used for manufacturing the fermented product. A microorganism capable of producing an acetic acid concentration of 70 mM or less in a bean extract medium when at least $1 \times 10^7$ cells/ml of the microorganism is cultured in the bean extract medium is preferably used. As such a microorganism, lactic acid-producing microorganisms such as microorganisms of the genera *Lactobacillus, Streptococcus, Lactococcus, Pediococcus,* and *Leuconostoc,* and microorganisms belonging to the genus *Bifidobacterium* are preferable, with microorganisms belonging to the genus *Bifidobacterium* being particular preferable. *Bifidobacterium•breve, Bifidobacterium•longum, Bifidobacterium•infantis, Bifidobacterium•adolescentis, Bifidobacterium•bifidum, Bifidobacterium•Anglatum,* and *Bifidobacterium•Catenulatum* can be given as specific examples of the above-mentioned microorganisms. Bean extracts may be fermented by mixed fermentation using several kinds of strains in combination or by continuous fermentation using several kinds of strains in combination. Microorganisms which can be used other than those mentioned above include bacteria belonging to Genus *Bacillus,* Genus *Acetobacter,* Genus *Gluconobacter,* and the like; yeasts belonging to Genus *Saccharomyces,* Genus *Candida,* Genus *Rhodotorula,* Genus *Pichia,* Genus *Schizosaccharomyces,* Genus *Torula,* Genus *Zygosaccharomyces,* and the like; and molds belonging to Genus *Aspergillus,* Genus *Eurotium,* Genus *Monascus,* Genus *Mucor,* Genus *Neurospora,* Genus *Penicillium,* Genus *Rhizopus,* and the like.

There are no specific limitations to the bean extracts used to obtain the above fermented products inasmuch as the bean extracts can react with the above microorganisms. For example, bean extracts obtained from soybean, black bean, broad bean, azuki bean, green bean, green pea, garbonzo bean, and the like can be used. Of these, the extract obtained from soybean is particular preferable. Any form of bean can be used for producing the bean extracts without specific limitations. Preferable forms are whole beans containing oils and fats, threshed beans, bean groats, bean flakes, and the like, with threshed beans being particularly preferable. Bean extracts produced by any process can be used. An example of the bean extract producing process comprises steps of immersing raw beans in water, adding hot water containing or not containing 0.5–1.0 wt % sodium carbonate, pulverizing the beans, removing bean curd refuse, and sterilizing the resulting product. Usually, bean extracts with a solid component of about 10 wt % are used.

Optionally, nutritive substances necessary for the growth of microorganisms such as saccharides used for food products, such as sucrose, glucose, fructose, and invert sugar, meat extracts, peptones, yeast extracts, and peptides may be added to the bean extracts prior to fermentation. Edible acids such as citric acid, malic acid, ascorbic acid, lactic acid, and acetic acid may be added to maintain the bean extract in a pH optimal to the growth of microorganisms.

There are no limitations to the method for causing the above-described microorganisms to react with the bean extract thus prepared. For example, a fluid of previously cultured microorganisms is inoculated in the bean extract and the mixture is stirred at a temperature for a period of time appropriate for growth of the microorganisms under suitable conditions for the microorganisms, for example, under anaerobic conditions, if the microorganism is anaerobic. Fermenting conditions suitable for incubation such as stationary culture, stirring culture, shaking culture, and aerobic culture can be employed.

The fermented product obtained in this manner is mixed with a lower alcohol such as ethanol or a polyhydric alcohol such as 1,3-butylene glycol, a pentylene glycol (e.g. 1,2-pentanediol), propylene glycol, glycerol, and isoprene glycol to remove high molecular weight substances by centrifuge, filtration, or other means.

The fermented product may be combined with vitamin A and/or a derivative thereof as is for use as a skin preparation for external application. However, the fermented product obtained by the subsequent deodorizing step to decrease the odor can also be used (such a fermented product is hereinafter referred to as "deodorized fermented product").

Specifically, the deodorized fermented product can be obtained by adding to the fermented product one or more members selected from the group consisting of a carbonate such as magnesium carbonate, calcium carbonate, zinc carbonate, nickel carbonate, barium carbonate, praseodymium carbonate, beryllium carbonate, magnesium calcium carbonate, radium carbonate, yttrium carbonate, cadmium carbonate, silver carbonate, chromium carbonate, cobalt carbonate, dysprosium carbonate, mercury carbonate, cerium carbonate, iron carbonate, copper carbonate, strontium carbonate, manganese carbonate, and lead carbonate and talc. The amount of carbonate and talc added to the fermented product can be appropriately determined in the range of 0.005–10 wt %, preferably 0.1–2.0 wt %, and more preferably 0.4–1.2 wt % of the fermented product.

A high deodorizing effect can be obtained if the product is allowed to stand for a prescribed period of time after completion of the deodorizing step. Although the period of time for which the product is allowed to stand is appropriately determined according to the degree of odor possessed by the fermented product, such a period of time is usually 5 hours or more, preferably 10–100 hours, more preferably 15–80 hours, and particular preferably 50–70 hours. Stirring the product during standing is a more preferable way of deodorization. In addition, if the product is allowed to stand at a temperature of 20° C. or less, and preferably 5° C. or less, or if the supernatant liquid is collected after standing with stirring, a deodorized fermented product having an even more reduced irritating odor and exhibiting a high stability with no degradation nor deposition of insoluble matters over a long period of time can be obtained.

Furthermore, other deodorizing steps may be combined with the above deodorizing step. For example, a fermented product with a reduced fermented odor and irritating odor, in particular, a product with a reduced soybean odor can be prepared by terminating production of acetic acid at an allowable level during the step of reacting microorganisms with a bean extract at a time sufficient for the product to have an adequate flavor and by adjusting the pH using an organic acid. In this step, although the allowable acetic acid concentration can be appropriately determined taking into consideration other flavoring additives to be added to the final product, the acetic acid concentration in the fermented product is 70 mM or less, preferably 50 mM or less, and more preferably 30 mM or less. Such an allowable acetic acid concentration can be judged by a pH of 4.5 or more, preferably 4.5–6.0, and still more preferably 5.0–6.0.

There are no specific limitations to the organic acid used for the pH adjustment inasmuch as the acid is an organic acid other than acetic acid that can be incorporated in a skin preparation for external application. Preferable organic acids are citric acid, lactic acid, malic acid, ascorbic acid, tartaric acid, gluconic acid, succinic acid, glutamic acid, and the like with lactic acid being particularly preferable. The target pH to be adjusted can be determined in a range in which the microorganism is stable. Usually, the pH is lowered as much as 0.1–2.5, and preferably as much as about 1.0, from the pH at which the fermentation was terminated. The pH is preferably adjusted so that the skin preparation for external application of the present invention ultimately has a pH in the range of 3.5–5.0.

A fermented product with a reduced soybean odor, fermented odor, and irritating odor can also be obtained by performing the process steps such as the step of causing the microorganisms to contact with the bean extract and/or the deodorizing step in a nitrogen atmosphere.

The amount of the fermented product or deodorized fermented product in the skin preparation of the present invention is not specifically limited. An amount usually added to a skin preparation for external application maybe used. For example, 0.0001–50%, preferably 0.01–20%, and particularly preferably 0.5–10% of the fermented product may be added.

Common vitamins abundantly contained in foods can be used as the vitamin A in the present invention. Vitamin A derivatives are compounds derived from the vitamin A. Both vitamin A and the derivatives are added to food and are highly stable compounds. Vitamin A and derivatives of Vitamin A used in the present invention include, but are not limited to, β-carotene and/or derivatives thereof, retinol, various fatty acid esters such as retinyl palmitate, retinyl stearate, and retinyl acetate, various organic acid esters of retinol such as retinyl lactate and retinyl glycolate, various inorganic acid diester composites of retinal such as inorganic acid diester of phosphoric acid, pyrophosphoric acid, or sulfuric acid. All-trans-retinol and isomers thereof, all-trans-retinoic acid and isomers thereof, all-trans-retinal and isomers thereof, as well as 3-dehydro isomers and 3,4-didehydro isomers of these vitamin A derivatives are preferable. Of the above vitamin A compounds, retinyl palmitate, which is readily available on the market and comparatively stable, is particularly preferably. Either synthesized or naturally occurring Vitamin A and/or the derivatives of Vitamin A may be used in the present invention. In the case of a naturally occurring Vitamin A or the derivatives, the material may be either crude or refined.

The Vitamin A and/or derivatives thereof may be used in a commonly used amount in the present invention without any specific limitation. For instance, retinol is used in the range of about 0.0001–10%, retinoic acid is used in the range of about 0.0001–10%, and retinyl palmitate is used in the range of about 0.0001–10%. The use of retinyl palmitate in the range of 0.01–1% is particularly preferable.

In addition to the above components, materials commonly used in preparing pharmaceuticals, quasi-drugs, cosmetics, bathing agents, food and beverages, and the like can be added in preparing the skin preparation for external use of the present invention. Examples of such commonly used materials include surfactants, oils, alcohols, humectants, thickeners, water-soluble polymers, antiseptics, antioxidants, chelating agents, pH regulators, foaming agents, perfumes, coloring matters, pigments, U absorbers and dispersants, fine particles, vitamins, amino acids, antibacterial agents, plant extracts, animal origin components, seaweed extracts, various chemicals, additives, and water.

The following compounds can be given as examples of the surfactants: nonionic surfactants such as sorbitanmonolaurate, sorbitan monopalmitate, sorbitan sesquioleate, sorbitan trioleate, polyoxyethylene sorbitan monolaurate, polyoxyethylene sorbitan monostearate, polyethylene glycol monooleate, polyethylene glycol alkylate, polyoxyethylene alkyl ether, polyglycol diether, lauroyl diethanolamide, fatty acid iso-propanolamide, maltitol hydroxy fatty acid ether, alkylated polysaccharide, alkyl glucoside, sugar ester, oleophillic glycerol monostearate, self-emulsifiable glycerol monostearate, polyglycerol monostearate, polyglycerol alkylate, sorbitan monooleate, polyethylene glycol monostearate, polyoxyethylene sorbitan monooleate, polyoxyethylene cetyl ether, polyoxyethylene sterol, polyoxyethylene lanolin, polyoxyethylene bees wax, and polyoxyethylene hydrogenated castor oil; anionic surfactants such as sodium stearate, potassium palmitate, sodium cetyl sulfate, sodium lauryl phosphate, sodium polyoxyethylene lauryl sulfate, triethanolamine palmitate, polyoxyethylene sodium lauryl phosphate, and sodium N-acyl glutamate; cationic surfactants such as stearyl dimethylbenzyl ammonium chloride, stearyl trimethyl ammonium chloride, benzalkonium chloride, and laurylamine oxide; amphoteric surfactants such as alkylaminoethyl glycine chloride and lecithin; and the like.

The following compounds can be given as examples of the oils: vegetable oils and fats such as macadamia nut oil, castor oil, olive oil, cacao oil, camellia oil, coconut oil, Japan wax, jojoba oil, grape seed oil, and avocado oil; animal oils and fats such as mink oil and egg yolk oil; waxes such as beeswax, whale wax, lanolin, carnauba wax, and candelila wax; hydrocarbons such as liquid paraffin, squalane, micro-crystallin wax, ceresin wax, paraffin wax, and Petrolatum jelly; natural and synthetic fatty acids such as lauric acid, myristic acid, stearic acid, oleic acid, isostearic acid, behenic acid, palmitic acid, capric acid, lanolin fatty acid, linolic acid, and linolenic acid; natural and synthetic higher alcohols such as cetyl alcohol, stearyl alcohol, hexyl decanol, octyl dodecanol, lauryl alcohol, capryl alcohol, myristyl alcohol, cetyl alcohol, cholesterol, and phytosterol; and esters such as isopropyl myristate, isopropyl palmitate, octyldodecyl myristate, octyldodecyl oleate, and cholesterol oleate.

As humectants, pentylene glycols such as glycerol, erythritol, xylytol, maltitol, propylene glycol, 1,3-butylene glycol, sorbitol, polyglycerol, polyethylene glycol, dipropylene glycol, and 1,2-pentane diol; polyhydric alcohols such as isoprene glycol; natural moisture factors (NMF) such as amino acids, sodium lactate, and sodium pyrrolidone carboxylate; and water-soluble high molecular weight compounds such as xyloglucan, queenseed, carageenan, pectin, mannan, curdlan, galactan, dermatan sulfate, glycogen, keratan sulfate, chondroitin, mucoitin sulfate, kerato sulfate, locust bean gum, succinoglucan, charonin acid, heparan sulfate, sodium hyaluronate, hyaluronic acid, collagen, mucopolysaccharides, and chondroitin sulfate; and the like can be given. polyvinyl alcohol, and acrylic acid-alkyl methacrylate copolymer; and the like can be given.

As the antiseptics, benzoate, salicylate, sorbate, dehydroacetate, p-oxybenzoate, 2,4,4'-trichloro-2'-hydroxydiphenyl ether, 3,4,4'-trichlorocarboanilide, benzalkonium chloride, hinokitiol, resorcin, ethanol, and the like can be given.

As examples of the antioxidants, dibutylhydroxytoluene, butylhydroxyanisole, propyl gallate, and ascorbic acid can be given. As examples of the chelating agents, edetate, pyrophosphate, hexametaphosphate, citrate, tartarate, and gluconate can be given. As examples of pH regulators, sodium hydroxide, triethanolamine, citric acid, sodium citrate, boric acid, borax, and potassium hydrogen phosphate can be given.

Examples of the UV absorbers and dispersants include p-aminobenzoic acid UV absorbers, anthranilic acid UV absorbers, salicylic acid UV absorbers, cinnamic acid UV absorbers, benzophenone UV absorbers, sugar UV absorbers, 3-(4'-methylbenzylidene)-d-camphor, 3-benzylidene-d, 1-camphor, uroxanic acid, ethyl uroxanate, 2-phenyl-5-methylbenzoxazol, 2-(2'-hydroxy-5'-t-octylphenyl) benzotriazol, 2-(2'-hydroxy-5'-methylphenyl)benzotriazole, dibenzaladine, dianisoyl methane, 4-methoxy-4'-t-butyldibenzoylmethane, 5-(3,3-dimethyl-2-norbornyliden)-3-pentan-2-on, 2-hydroxy-4-methoxybenzophenone, octyldimethyl p-aminobenzoate, ethylhexyl p-methoxycinnamate, titanium oxide, kaolin, and talc.

As vitamins, vitamin Bs such as vitamin $B_6$ hydrochloride, vitamin $B_6$ tripalmitate, vitamin $B_6$ dioctanoate, vitamin $B_2$ and the derivatives thereof, vitamin $B_{12}$, and vitamin $B_{15}$ and the derivatives; vitamin Cs such as ascorbic acid, ascorbic sulfate and the salt thereof, ascorbic phosphate and the salt thereof, ascorbic acid dipalmitate, ascorbic acid glucoside, acyl ascorbic acid glucoside, and ascorbic acid tetraisopalmitate; vitamin D; vitamin Es such as α-tocopherol, β-tocopherol, γ-tocopherol, and vitamin E acetate; vitamin F, vitamin K, pantothenic acid, pantethine, vitamin H, vitamin P, vitamin U, carnitine, ferulic acid, γ-oryzanol, α-lipoic acid, orotic acid, and derivatives of these vitamin compounds.

As amino acids, glycine, alanine, valine, leucine, isoleucine, serine, threonine, phenylalanine, thyrosin, asparagine, glutamine, taurine, tryptophan, cystine, cysteine, methionine, proline, hydroxyproline, aspartic acid, glutamic acid, arginine, histidine, lysine, derivatives of these amino acids, and the like can be given. gardeniae fructus, scutellaria, liquorice, artemisia capillaris, sophorae radix, cocis semen, lonicera periclymenum, peony root, mori cortex, hawthorn, moutan cortex, and cepharanthin can be given.

As seaweed extracts, brown alga such as sea tangle, *Laminaria japonica, Underaia pinnatifida, Sargassum fusiforme Setchell, Ascophyllum nodosum, Fucales, Nemacystus decipiens Kuckuck, Cladosiphon okamuranus Tokida*, and *Himanthalia elongata*; red algae such as *Gelidiaceae, Corallinaceae, Palmaria, Chondrus ocellatus*, and *Laver* can be given.

As various chemicals which can be added to the skin preparation of the present invention, nicotinamide, benzyl nicotinate, γ-oryzanol, allantoin, glycyrrhizic acid and salts thereof, glycyrrhetinic acid and derivatives thereof, hinokitiol, bisabolol, eucalyptol, timor, and inositol; saponins such as saikosaponin, carrot saponin, loofah saponin, and Sapindaceae saponin; pantothenyl ethyl ether, ethynyl estradiol, tranexamic acid, arbutin, placenta extract, and the like can be given.

The skin preparation for external application of the present invention may have various forms such as a cosmetic preparation, medicinal preparation, and quasi-drug preparation. These preparations are manufactured according to conventional methods. Specific products include face lotion, milky lotion, moisture retention cream, cleansing cream, massage cream, medicated patch, facial washing cream, pack, essence, and ointment; finishing cosmetics such as foundation, lipstick, mascara, and eye shadow; hair cosmetics such as shampoo, rinse, treatment, hair tonic, hair liquid, hair cream, and hair milk; after-shave lotion, body soap, and bath agent; and the like.

EXAMPLES

The present invention will be described in more detail by way of preparation examples, test examples, and examples which should not be construed as limiting the present invention.

Preparation Example 1

(1) Preparation of Fermented Product

Soybeans were washed with water and soaked in water overnight to sufficiently absorb water. After adding water in an amount of four times that of the soybeans, the soybeans were crushed into a paste using a mixer. The paste was heated at 100° C. for 30 minutes, cooled, and filtered. The filtrate was sterilized with steam at 100° C. for 90 minutes to obtain soybean milk with a solid content of about 10 wt %.

After inoculating previously cultured broth of *Bifidobacterium breve* YIT 4065 (FERM BP-6223) in the amount of 0.5% of the total amount of the soybean milk, the mixture was incubated for 24 hours at 37° C. to obtain fermented soybean milk. The number of live microorganisms in the resulting fermented soybean milk was $1.3 \times 10^9$ cells/ml. An equivalent amount of ethanol was added to the fermented soybean milk and the mixture was filtered to obtain a fermented product (hereinafter referred to as "SB") 1.

Preparation Example 2

(2) Preparation of Fermented Product

A previously cultured broth of *Bifidobacterium breve* YIT 4065 (FERM BP-6223) was inoculated in soybean milk prepared in the same manner as in Preparation Example 1 to make the concentration of the cultured broth in the soybean milk 1.0%. The mixture was incubated at 30° C. in a nitrogen atmosphere until the culture broth became pH 5.5. After adjusting to pH 4.5, the culture broth was incubated for a further 26 hours at 37° C. The number of live microorganisms in the resulting fermented soybean milk was $4.2 \times 10^8$ cells/ml. 1,3-butylene glycol in an amount of three times that of the fermented soybean milk was added and the mixture was filtered to obtain a fermented product 2.

Test Example 1

The Measurement Cell Activation Effect by Cell Culture (1)
(Cell Culture)

Immortalized cells obtained by transforming human epidermic cells (manufactured by Kurabo Industries, Ltd.) using SV40 virus T antigen according to the method of Yasumoto et al. (Cultured Cell Experiment For Molecular Biology Research by S. Yasumoto, edited by T. Kuroki et al., Yodosha Co., Ltd., 1995, pp 191–200) were used as test cells. The cells were disseminated in a 96 well plate ($4 \times 10^3$ cells/0.1 ml/well) and cultured in a serum-free liquid medium for proliferation (HuMedia-KG 2: Kurabo Industries, Ltd.) under the conditions of 37° C. and a $CO_2$ concentration of 5%. After culturing for one day, the culture medium was replaced with a medium to which the fermented product 1 prepared in the Preparation Example 1 and all-trans-retinol (manufactured by Sigma Co., hereinafter abbreviated from time to time as "ROH") as a vitamin A and/or derivative thereof were added, followed by culturing for a further two days. The cells were also cultured in media to which the above components were individually added as Comparative Examples, and in a medium to which none of these components were added as a control.

(Method of Measuring Cell Activation Effect)

On the third day of culturing, a reducing-type coloring reagent (WST-1, manufactured by Dojindo Co.) was added in an amount of 10 μl/well, followed by incubation for 2 hours under the conditions of 37° C. and a $CO_2$ concentration of 5%. Then, absorption at 450–660 nm was measured. Metabolic activity of the cells was calculated from the resulting absorbance. The cell activation effect was evaluated from the rate of increase in the metabolic activity in comparison with the control sample. The results are shown in FIG. 1.

It can be seen from FIG. 1 that the experiment (SB+ROH), in which the 0.5% fermented product 1 (SB) and $5 \times 10^{-9}$ M all-trans-retinol (ROH) were used, each at a concentration at which these components cannot exhibit metabolic activity if used alone, showed a significant increase in metabolic activity of human epidermic cells as compared with the experiments (SB or ROH) in which these components were individually used, demonstrating a synergistic cell activation effect of these components.

Test Example 2

The Measurement Cell Activation Effect by Cell Culture (2)

The effect of the combined use of the fermented product 1 and all-trans-retinoic acid (Sigma Co., hereinafter abbreviated from time to time as "RA") on metabolic activity of human epidermic cells was examined in the same manner as in the Test Example 1, except for using the all-trans-retinoic acid as the vitamin A and/or the derivative. The results are shown in FIG. 2.

Figure 2:
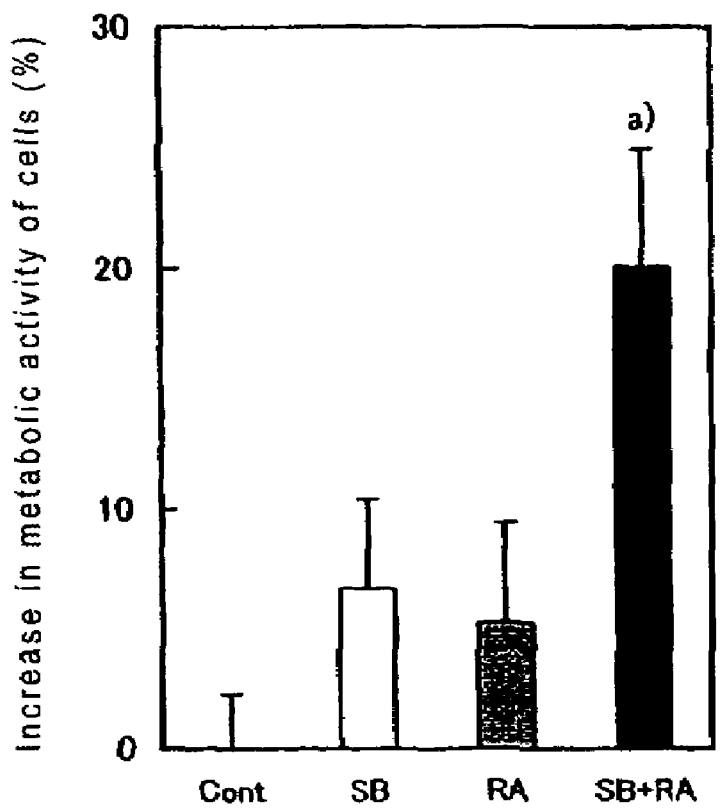
FIG. 2 shows the effect of the combined use of the fermented product 1 (SB) and all-trans-retinoic acid (RA) on the metabolism activity of incubated human epidermic cells.

It can be seen from FIG. 2 that the experiment (SB+RA), in which the 0.5% fermented product 1 (SB) and $5 \times 10^{-10}$ M all-trans-retinoic acid (RA) were used, each at a concentration at which these components cannot exhibit metabolic activity if used alone, showed a significant increase in metabolic activity of human epidermic cells as compared with the experiments (SB or RA) in which these components were individually used, demonstrating a synergistic cell activation effect of these components.

Test Example 3

Promotion of Hyaluronic Acid Production by Cell Culture (1)

Cells were cultured in the same manner as in Test Example 1. A supernatant liquid was collected on the third day of culturing for determination of the amount of hyaluronic acid by a method similar to the ELISA method (Fosang A. J. et al., Matrix 10, 306–313, 1990) using a biotin-labeled hyaluronic acid-bonding protein (Seikagaku Corp.). The effect of combined use of the fermented product 1 and all-trans-retinol on hyaluronic acid production by human epidermic cells was examined by determining the relative amount (%) of hyaluronic acid to the control (taking the hyaluronic acid concentration of the control to which no samples was added as 100) in the sample in which the 0.5% fermented product 1 and $5 \times 10^{-9}$ M all-trans-retinol were added and in the samples in which each of these components were individually added. The results are shown in FIG. 3.

Figure 3:
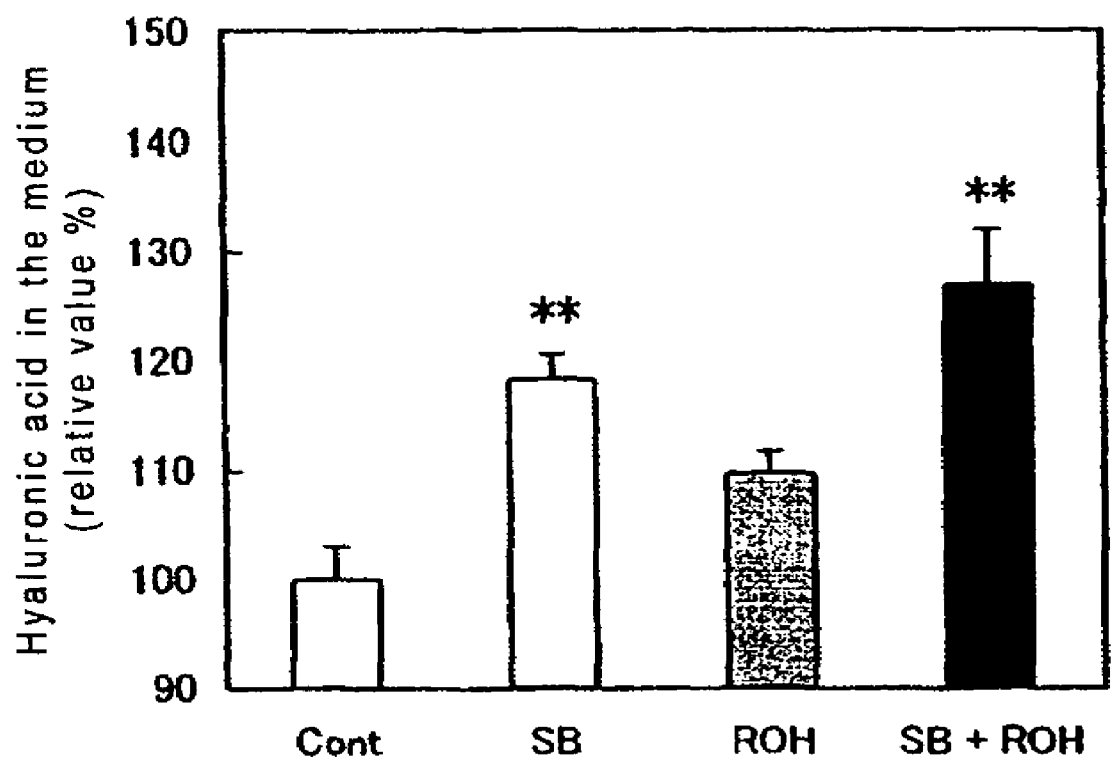
FIG. 3 shows the effect of the combined use of the fermented product 1 (SB) and all-trans-retinol (ROH) on hyaluronic acid production by incubated human epidermic cells.

FIG. 3 shows the synergistic effect of the fermented product 1 and the all-trans-retinol on hyaluronic acid production by human epidermic cells.

Test Example 4

Promotion of Hyaluronic Acid Production by Cell Culture (2)

The effect of the combined use of the fermented product 1 and all-trans-retinoic acid on hyaluronic acid production by human epidermic cells was examined in the same manner as in the Test Example 3, except for using $5 \times 10^{-10}$ M all-trans-retinoic acid as the vitamin A and/or the derivative. The results are shown in FIG. 4.

Figure 4:
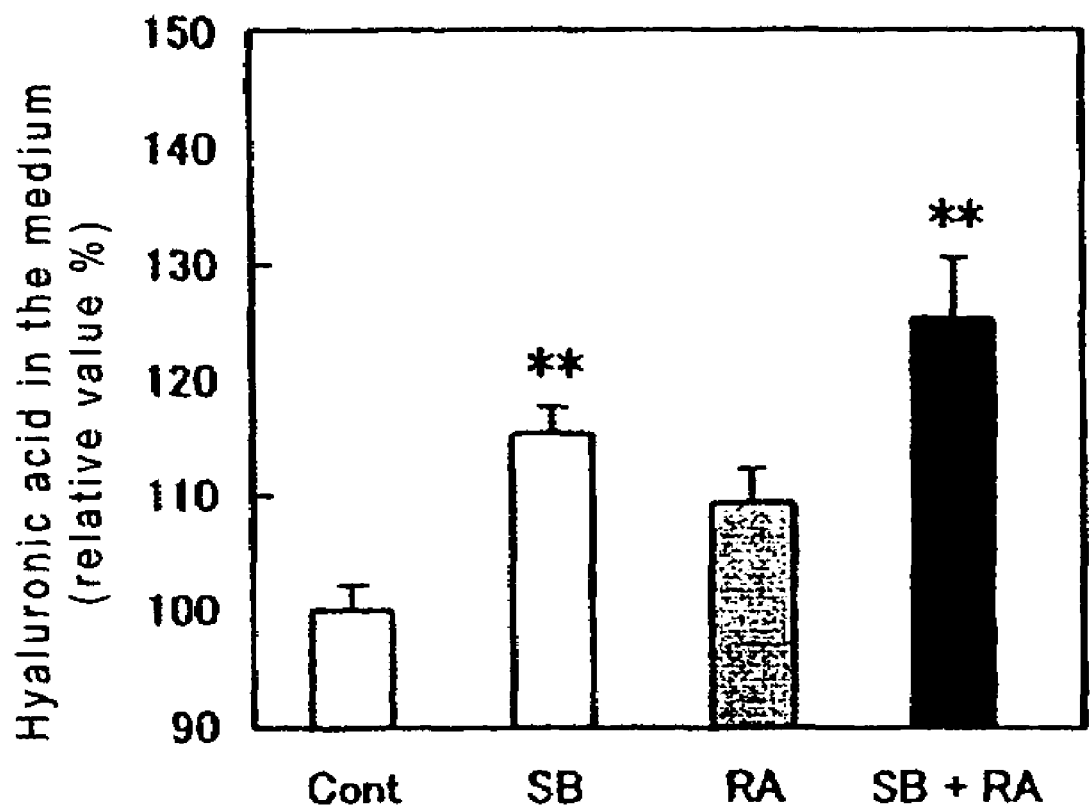
FIG. 4 shows the effect of the combined use of the fermented product 1 (SB) and all-trans-retinoic acid (RA) on hyaluronic acid production by incubated human epidermic cells.

FIG. 4 shows the synergistic effect of the fermented product 1 and the all-trans-retinoic acid on hyaluronic acid production by human epidermic cells.

Test Example 5

Wrinkle Improvement Test

Five female panelists having wrinkles on the face used the essence with the following formulation comprising the fermented product 2 and retinyl palmitate for 3 months. The method of Hayashi (Hayashi S., Fragrance Journal, 11, 55–61, 1992) with modification was applied to the evaluation of wrinkles. Specifically, skin replicas of the cheek were produced before and after the test period using a fast-dry opaque silicone rubber (Silflo, manufactured by Flexico Developments Co.) to determine the maximum depth of wrinkles using an image analyzer (ASPECT, manufactured by Mitani Corp.). The wrinkle improvement was indicated as the ratio (in percentage) of the maximum depth of wrinkles after the test period to the maximum depth of wrinkles before the test period. The results are shown in FIG. 5.

| Component | (wt %) |
| --- | --- |
| Ethanol | 10.0 |
| Fermented product 2* | 5.0 |
| 1,3-Butylene glycol | 3.0 |
| Trimethyl glycine | 1.0 |
| Purified water | Balance |
| Carboxy vinyl polymer | 0.1 |
| Carageenan | 0.1 |
| Glycerol | 5.0 |
| Squalane | 1.0 |
| Methylphenyl polysiloxane | 1.0 |
| Polymethacryloyloxyethyl phosphoryl choline solution | 2.0 |
| Behenyl alcohol | 0.1 |
| Polyoxyethylene sorbitan monostearate | 0.2 |
| Glycerol monostearate | 0.1 |
| Retinyl palmitate | 0.01 |
| Stearyl glycyrrhizinate | 0.1 |
| Methyl parabene | 0.1 |
| Perfume | 0.1 |
| Sodium hydroxide | Appropriate amount |

*The product of preparation Example 2.

Figure 5:
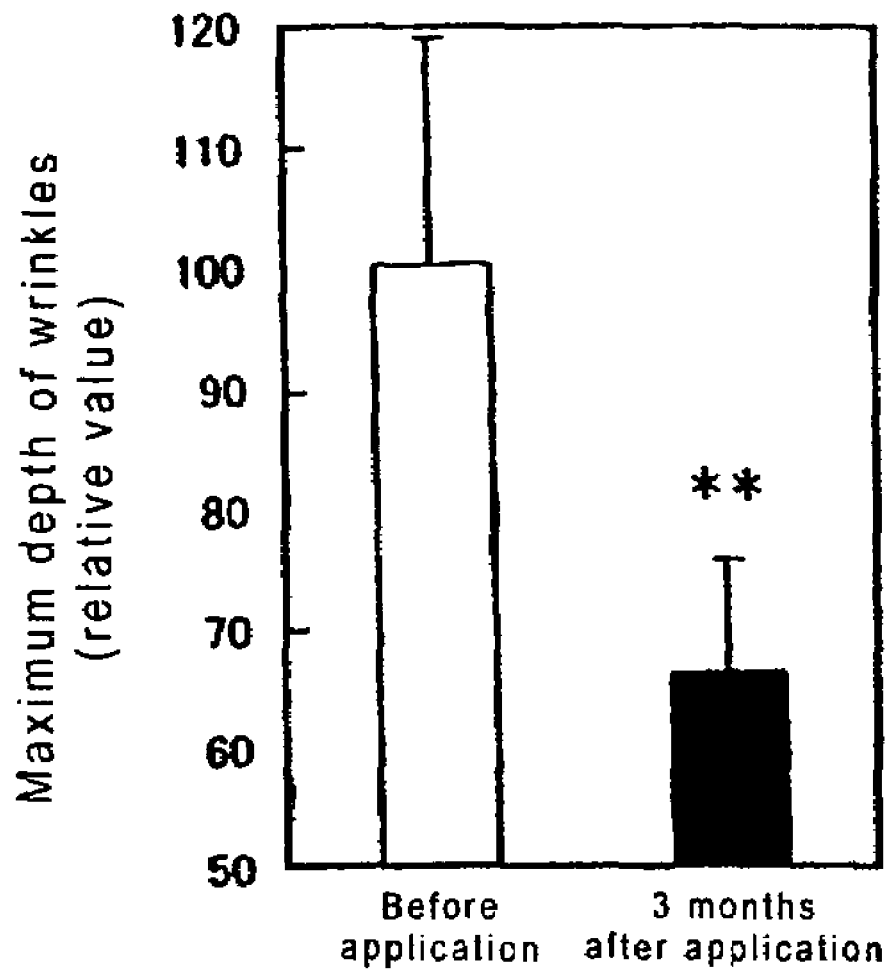
FIG. 5 shows the effect of an essence comprising a fermented product 2 and retinyl palmitate on wrinkles on the human face.

The results of FIG. 5 shows that the maximum depth of wrinkles of the human face has decreased about 35% during the external application of the sample composition for 3 months, indicating the wrinkle improving effect of the essence comprising the fermented product and retinal palmitate.

Test Example 6

Skin Elasticity Improvement Test

Ten healthy females applied the essence of Test Example 5 to the face for 3 months. Skin elasticity on the face was measured before and after the test period according to the method of Takema (Takema Y et al., Br. J. Dermatol. 131, 641–648, 1994). Specifically, a load of 300 mbar was applied to the face for 2 seconds and the elasticity of the skin was (skin elasticity, R2 relative value) measured at 2 seconds after release of the load using a cutometer SEM575 with a probe diameter of 2 mm (manufactured by Courage and Khazaka Co.). The relative skin elasticity was determined using the skin elasticity before the test period as 100%. The results are shown in FIG. 6.

Figure 6:
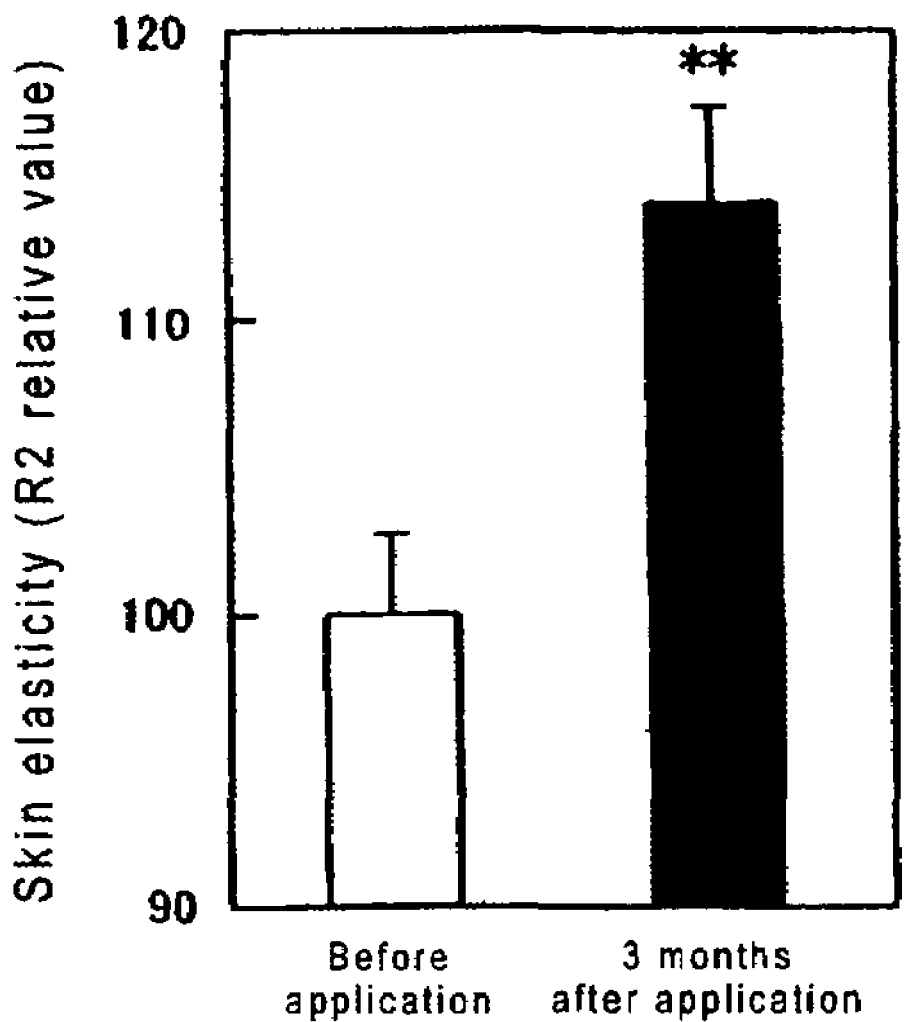
FIG. 6 shows the effect of an essence comprising the fermented product 2 and retinyl palmitate on elasticity of the skin of the human face.

It can be seen from the results of FIG. 6 that the skin elasticity increased about 15% by external application of the essence to which the fermented product and retinyl palmitate were added for 3 months. The essence has been proven to improve elasticity of the skin that is known to decrease by aging (Takema Y. et al., Br. J. Dermatol. 131, 641–648, 1994).

Test Example 7

Measurement of Water Content in Horny Cell Layer

Ten healthy females applied the essence of Test Example 4 to the face for 3 months. The water content in the horny cell layer (conductance) of the face was measured before and after the application according to a conventional method using a conductance meter (SKICON 200, manufactured by IBS Corp.). The results are shown in FIG. 7.

Figure 7:
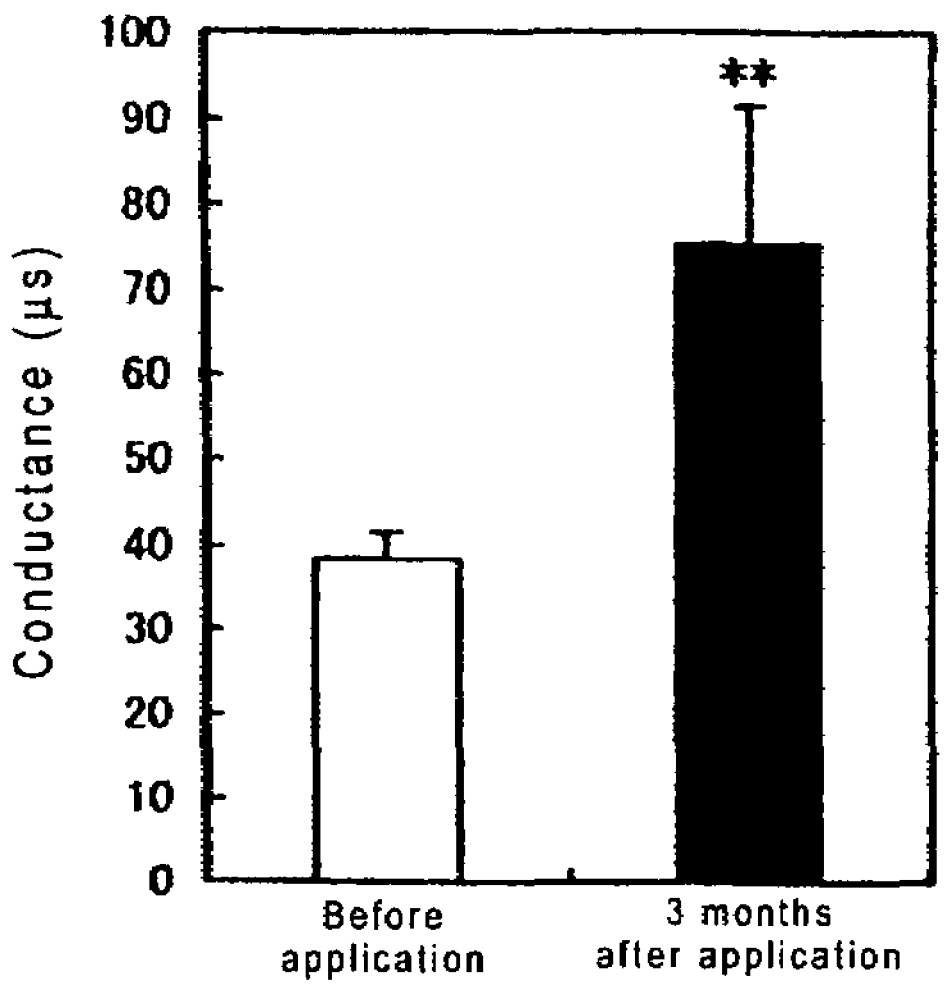
FIG. 7 shows the effect of an essence comprising the fermented product 2 and retinyl palmitate on the water content of the horny cell layer of the human face.

It can be seen from the results of FIG. 7 that the conductance increased about two times by external application for 3 months of the essence to which the fermented product and retinyl palmitate were added. The essence thus has been proven to exhibit a moisturizing effect.

Preparation Example 3

Preparation of Fermented Product (3)

A previously cultured broth of *Bifidobacterium breve* YIT 4065 (FERM BP-6223) was inoculated in soybean milk prepared in the same manner as in Preparation Example 1 to make the concentration of the cultured broth in the soybean milk 0.5%. The mixture was incubated stationarily at 37° C. for 24 hours to obtain a fermented soybean milk. The number of live cells in the resulting fermented soybean milk was $1.3 \times 10^9$ cells/ml. 1,3-butylene glycol in an amount of three times that of the fermented soybean milk was added and the mixture was stirred. After one day, the mixture was filtered to obtain a fermented product 3.

Preparation Example 4

Preparation of Fermented Product (4)

A previously cultured broth of *Bifidobacterium breve* YIT 4065 (FERM BP-6223) was inoculated in soybean milk prepared in the same manner as in Preparation Example 1 to make the concentration of the cultured broth in the soybean milk 1.0%. The mixture was stationarily incubated at 34° C. for 23 hours. When the culture broth became pH 5.5, lactic acid was added to make pH 4.4, followed by stationary incubation at 34° C. for a further 22 hours. The number of live cells was $7.3 \times 10^8$ cell/ml. After incubation, 1,3-butylene glycol in an amount of three times that of the fermented soybean milk was added and the mixture was stirred. After one day, the mixture was filtered to obtain a fermented product 4.

Test Example 8

Water Retention and Deodorizing Effects of Fermented Product (1)

Samples were prepared by adding magnesium carbonate, calcium carbonate, talc, activated carbon, or diatomaceous earth to the fermented product 2 prepared in the Preparation Example 2, each to a concentration of 0.8%, stirring the mixture for 68 hours at room temperature, allowing the mixture to stand, and filtering. The contents of lactic acid, acetic acid, sucrose, and isoflavone were determined. The results were indicated as the ratio (in percentage) of these components in each sample to the amount in the additive-free sample. For the determination of pH, each sample was mixed with water to make a 10% aqueous solution.

To evaluate the effect of decreasing an irritating odor, each sample was applied to the inside of the forearm of 20 male and female adult panelists. The sensation was scored according to the standard in Table 1. The average of scores was determined. The skin moisturizing effect on the human skin of each sample was also examined. To evaluate the moisturizing effect, a 10% aqueous solution of each sample was applied to the inside of the cleaned forearm of five panelists to measure the amount of water after 30 minutes using a conductance meter (SKICON 200, manufactured by IBS Corp.). Average of the water content was determined for comparison. The results are shown in Table 2.

TABLE 1

| Sensation | Score |
| --- | --- |
| Excellent (no irritating odor) | ±0 |
| Good (irritating odor is not unpleasant) | −1 |
| Slightly unpleasant odor | −2 |
| Unpleasant odor (irritating odor) | −3 |
| Significantly unpleasant odor (strong irritating odor) | −4 | was particularly high. There were no changes in the amounts of lactic acid, acetic acid, sucrose, and isoflavone. The water content in the horny layer also did not change.

Test Example 9

Moisturizing and Deodorizing Effects of Fermented Product (2)

Magnesium carbonate was added to the fermented product 2 prepared in the Preparation Example 2 to a final concentration of 0, 0.005, 0.01, 0.1, 0.4, 0.8, 1.2, 2.0, or 10.0%, the mixture was stirred for 24 hours at room temperature, allowed to stand, and filtered to obtain samples. The lactic acid, acetic acid, sucrose, and isoflavone content and pH of each sample were determined. Each sample was applied to the inside of the forearm of 20 male and female adult panelists to examine the deodorizing effect and the water content in the horny cell layer in the same manner as in Test Example 8. The results are shown in Table 3.

TABLE 2

| | Substance | Lactic acid (%) | Acetic acid (%) | Sucrose (%) | Isoflavone (%) | Deodorizing effect | Water (µs) | pH |
| --- | --- | --- | --- | --- | --- | --- | --- | --- |
| Test product 1 | Additive free | 100.0 | 100.0 | 100.0 | 100.0 | −3.08 | 86 | 4.21 |
| Test product 2 | Activated carbon | 91.7 | 100.0 | 96.8 | 96.9 | −3.02 | 84 | 4.23 |
| Test product 3 | Diatomaceous earth | 91.7 | 100.0 | 96.8 | 100.0 | −3.04 | 85 | 4.78 |
| Test product 4 | Magnesium carbonate | 91.7 | 100.0 | 96.8 | 100.0 | −0.36 | 87 | 5.90 |
| Test product 5 | Calcium carbonate | 91.7 | 100.0 | 96.8 | 100.0 | −0.52 | 86 | 5.78 |
| Test product 6 | Talc | 91.7 | 100.0 | 96.8 | 100.0 | −1.72 | 86 | 4.47 |

The results of Table 2 show that a deodorizing effect can be obtained by the addition of magnesium carbonate, calcium carbonate, or talc. The effect of magnesium carbonate

TABLE 3

| | Magnesium carbonate (%) | Lactic acid (%) | Acetic acid (%) | Sucrose (%) | Isoflavone (%) | Deodorizing effect | Water (µS) | pH |
| --- | --- | --- | --- | --- | --- | --- | --- | --- |
| Test product 1 | 0 | 100.0 | 100.0 | 100.0 | 100.0 | −3.08 | 86 | 4.21 |
| Test product 7 | 0.005 | 91.7 | 100.0 | 96.8 | 100.0 | −2.08 | 84 | 4.22 |
| Test product 8 | 0.01 | 91.7 | 100.0 | 96.8 | 100.0 | −1.14 | 86 | 4.30 |
| Test product 9 | 0.1 | 91.7 | 100.0 | 96.8 | 100.0 | −0.76 | 85 | 5.02 |
| Test product 10 | 0.4 | 91.7 | 100.0 | 96.8 | 100.0 | −0.54 | 87 | 5.51 |
| Test product 11 | 0.8 | 91.7 | 100.0 | 96.8 | 100.0 | −0.36 | 87 | 5.90 |
| Test product 12 | 1.2 | 91.7 | 100.0 | 96.8 | 96.9 | −0.48 | 86 | 6.33 |

TABLE 3-continued

|  | Magnesium carbonate (%) | Lactic acid (%) | Acetic acid (%) | Sucrose (%) | Isoflavone (%) | Deodorizing effect | Water (μS) | pH |
|---|---|---|---|---|---|---|---|---|
| Test product 13 | 2.0 | 91.7 | 100.0 | 93.5 | 93.8 | −0.40 | 85 | 6.90 |
| Test product 14 | 10.0 | 83.3 | 80.0 | 90.3 | 93.8 | −0.52 | 83 | 7.50 |

The results of Table 3 show the addition of magnesium carbonate to a concentration of 0.01–10% had almost no effect on the content of lactic acid, acetic acid, sucrose, and isoflavone nor on the water content of the horny layer, but exhibited a deodorizing effect. The addition of magnesium carbonate to a concentration exceeding 10% makes the composition with a pH greater than 7, resulting in instability such as deposition of insoluble matters and the like.

Test Example 10

Deodorizing Effect of Fermented Product

Magnesium carbonate was added to the fermented products 2–4 prepared in the Preparation Examples 2–4 to a final concentration of 0% or 0.6%. The mixture was stirred for 68 hours at 18° C. or less, allowed to stand, and filtered. The contents of lactic acid, acetic acid, sucrose, and isoflavone of each sample thus obtained were determined. The deodorizing effects were evaluated in the same manner as in Test Example 8. The results are shown in Table 4.

magnesium carbonate. In addition, a higher deodorizing effect was confirmed by replacing the step described in Preparation Example 3 by the step described in Preparation Example 4. The use of the step of Preparation Example 2 brought about a further deodorizing effect.

Test Example 11

Examination of Destabilization of Fermented Product

Magnesium carbonate was added to the fermented product obtained in Preparation Example 2 to make a final concentration of 0.6%. After the addition, the mixture was stirred for 68 hours at 25° C., 15° C., 10° C., and 5° C., allowed to stand, and filtered. The contents of lactic acid, acetic acid, sucrose, isoflavone, and water of each sample were determined in the same manner as in Test Example 8. After storing the samples for one month at 5° C., the absorbance of each sample at 400 nm was measured at 5° C. using a spectrophotometer. The results are shown in Table 5.

TABLE 4

|  | Fermented product | Magnesium carbonate (%) | Lactic acid (%) | Acetic acid (%) | Sucrose (%) | Isoflavone (%) | Deodorizing effect |
|---|---|---|---|---|---|---|---|
| Test product 1 | Fermented product 2 | 0 | 100.0 | 100.0 | 100.0 | 100.0 | −3.08 |
| Test product 15 |  | 0.6 | 91.7 | 100.0 | 96.8 | 100.0 | −0.45 |
| Test product 16 | Fermented product 3 | 0 | 52.5 | 158.0 | 101.9 | 99.4 | −3.88 |
| Test product 17 |  | 0.6 | 52.3 | 158.0 | 96.8 | 99.2 | −1.92 |
| Test product 18 | Fermented product 4 | 0 | 90.5 | 108.4 | 102.6 | 99.7 | −3.39 |
| Test product 19 |  | 0.6 | 90.5 | 108.3 | 98.4 | 99.6 | −1.37 |

It can be seen from the results of Table 4 that all samples exhibited a high deodorizing effect by the addition of Instability due to undesirable deposition was evaluated by the degree of opaqueness.

TABLE 5

|  | Magnesium carbonate (%) | Temperature (° C.) | Lactic acid (%) | Acetic acid (%) | Sucrose (%) | Isoflavone (%) | Deodorizing effect | Absorption (400 nm) | Water (μS) |
|---|---|---|---|---|---|---|---|---|---|
| Test product 1 | 0 | 25 | 100.0 | 100.0 | 100.0 | 100.0 | −3.08 | 1.0 | 86 |
| Test product 20 | 0.6 | 25 | 91.7 | 100.0 | 96.8 | 100.0 | −0.45 | 1.0 | 87 |
| Test product 21 | 0.6 | 15 | 91.6 | 100.0 | 96.8 | 99.9 | −0.47 | 0.7 | 85 |

TABLE 5-continued

| | Magnesium carbonate (%) | Temperature (° C.) | Lactic acid (%) | Acetic acid (%) | Sucrose (%) | Isoflavone (%) | Deodorizing effect | Absorption (400 nm) | Water (μS) |
|---|---|---|---|---|---|---|---|---|---|
| Test product 22 | 0.6 | 10 | 91.6 | 100.0 | 96.7 | 99.9 | −0.46 | 0.6 | 86 |
| Test product 23 | 0.6 | 5 | 91.5 | 100.0 | 96.6 | 99.8 | −0.42 | 0.4 | 87 |

It can be seen from the results of Table 5 that all samples exhibited a high deodorizing effect. In addition, an operation of stirring the sample and allowing it to stand thereafter at a temperature of 15° C. or less was confirmed to suppress deposition of insoluble matters and increase stability.

Preparation Example 5

Preparation of Fermented Product (5)

A previously cultured broth of *Bifidobacterium breve* YIT 4065 (FERM BP-6223) was inoculated in soybean milk prepared in the same manner as in Preparation Example 1 to make the concentration of the cultured broth in the soybean milk 0.5%. The mixture was stationarily incubated at 37° C. for 24 hours to obtain a fermented soybean milk. The number of live cells in the resulting fermented soybean milk was $1.3 \times 10^9$ cells/ml. Ethanol in the amount of three times the amount of the fermented soybean milk was added. The mixture was stirred and filtered. Fermented product 5 was prepared by adding magnesium carbonate to a concentration of 0.6%, stirring the mixture, allowing the mixture to stand for 24 hours at room temperature, and filtering.

Test Example 12

Promotion of Hyaluronic Acid Production by Cell Culture (3)

The effect of the combined use of the fermented product 5 (SBZ) and all-trans-retinol was examined in the same manner as in Test Example 3. The results are shown in FIG. 8.

Figure 8:
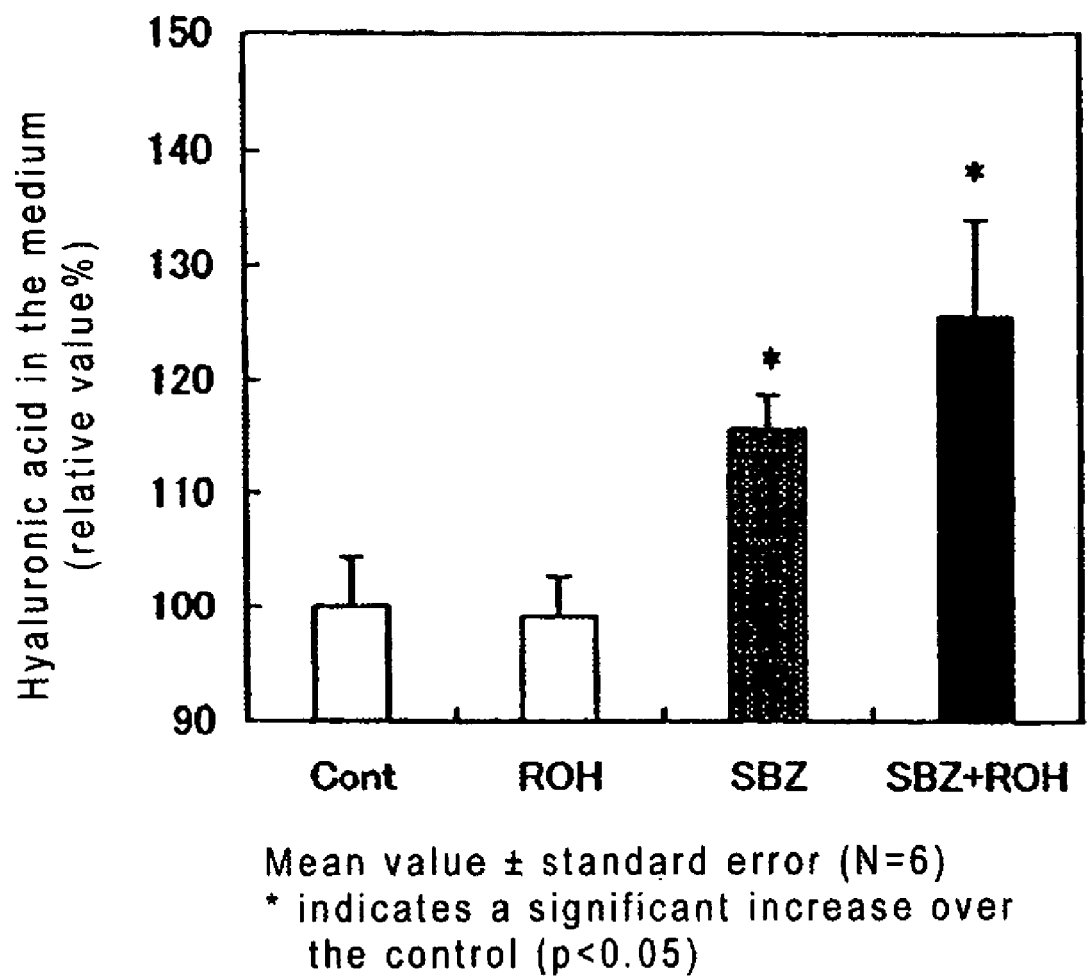
FIG. 8 shows the effect of the combined use of a fermented product 5 (SBZ) and all-trans-retinol (ROH) on hyaluronic acid production by incubated human epidermic cells.

FIG. 8 shows the synergistic effect of the fermented product and the all-trans-retinol on hyaluronic acid production by human epidermic cells.

Example 1

Lotion (1)

A lotion of the following composition was prepared.

| Component | (wt %) |
|---|---|
| Fermented product 1* | 10.0 |
| Retinyl palmitate | 0.01 |
| Ethanol | 5.0 |
| 1,3-Butylene glycol | 2.0 |
| Polyoxyethylene (50 E.O.) hydrogenated castor oil | 0.05 |
| Methyl paraoxybenzoate | 0.1 |
| Perfume | 0.1 |
| Purified water | Balance |

*The product of Preparation Example 1

The lotion obtained was excellent in preventing and improving skin roughness and imparted a refreshing sensation upon use. Storage stability was also excellent.

Example 2

Milky Lotion

A milky lotion of the following composition was prepared.

| Component | (wt %) |
|---|---|
| Fermented product 2* | 10.0 |
| Retinyl palmitate | 0.02 |
| Stearic acid | 2.0 |
| Liquid paraffin | 6.0 |
| Squalane | 2.0 |
| Sorbitan monostearate | 1.5 |
| Polyoxyethylene (20 E.O.) sorbitan monostearate | 2.0 |
| Methyl paraoxybenzoate | 0.05 |
| Glycerol | 1.0 |
| Perfume | 0.15 |
| Purified water | Balance |

*The product of Preparation Example 2

The milky lotion obtained was excellent in the cornification improving effect, skin elasticity improving effect, and moisturizing effect and imparted a moist sensation upon use. Storage stability was also excellent.

Example 3

Cream

A cream of the following composition was prepared.

| Component | (wt %) |
|---|---|
| Fermented product 2* | 10.0 |
| Retinyl palmitate | 0.05 |
| Liquid paraffin | 23.0 |
| Petroleum jelly | 7.0 |
| Behenyl alcohol | 1.0 |
| Stearic acid | 2.0 |
| Bees wax | 2.0 |
| Sorbitan monostearate | 1.5 |
| Polyoxyethylene (20 E.O.) sorbitan monostearate | 2.5 |
| Butyl paraoxybenzoate | 0.05 |
| Glycerol | 2.0 |
| Methyl paraoxybenzoate | 0.1 |
| Perfume | 0.15 |
| Purified water | Balance |

*The product of Preparation Example 2

The cream obtained was excellent in preventing and improving skin roughness and improving wrinkles, and imparted a comfortable sensation upon use. Storage stability was also excellent.

Example 4

Ointment

An ointment of the following composition was prepared.

| Component | (wt %) |
| --- | --- |
| Fermented product 2* | 10.0 |
| Retinyl palmitate | 0.05 |
| Hydrophilic ointment of Japanese Pharmacopoeia | 89.95 |

*The product of Preparation Example 2

The ointment was applied to the skin (5 mg/cm$^2$) twice a day to confirm excellent effect of preventing and improving skin roughness and excellent wrinkle improving effect. The storage stability was also excellent.

Example 5

Lotion (2)

A lotion of the following composition was prepared.

| Component | (wt %) |
| --- | --- |
| Fermented product 5* | 10.0 |
| Retinyl palmitate | 0.01 |
| Ethanol | 5.0 |
| 1,3-Butylene glycol | 2.0 |
| Polyoxyethylene (50 E.O.) hydrogenated castor oil | 0.05 |
| Methyl paraoxybenzoate | 0.1 |
| Perfume | 0.1 |
| Purified water | Balance |

*The product of Preparation Example 5

The lotion obtained was excellent in preventing and improving skin roughness and imparted a refreshing sensation upon use. Storage stability and fragrance was also excellent.

Reference Example 1

Lotion (1)

A lotion of the following composition was prepared.

| Component | (wt %) |
| --- | --- |
| Fermented product* | 10.0 |
| Ethanol | 8 |
| Pentylene glycol | 2 |
| Methyl parabene | 0.05 |
| Polyoxyethylene hydrogenated castor oil | 0.5 |
| Carboxyvinyl polymer | 0.1 |
| Perfume | 0.05 |
| Purified water | Balance |

*Test product 21

Reference Example 2

Lotion (2)

A lotion of the following composition was prepared.

| Component | (wt %) |
| --- | --- |
| *Lactobacillus* culture broth | 30 |
| Fermented product* | 1 |
| Sodium hydroxide | Appropriate amount |
| Ethanol | 8 |
| Perfume | 0.1 |
| Purified water | Balance |
| Talk | 0.1 |
| Polyoxyethylene (24) cholesteryl ether | 0.1 |
| Acetic acid-dl-α-tocopherol | 0.1 |
| Pentylene glycol | 30 |
| Methyl parabene | 0.1 |
| EDTA-2Na | 0.1 |
| Glycerol | 5 |
| Mori cortex extract | 0.1 |
| Dipotassium glycyrrhizate | 0.1 |
| Glycolic acid | 3 |
| Lactic acid | 3 |
| Sodium hyaluronate | 0.1 |
| dl-malic acid | 0.1 |

*Test product 21

Reference Example 3

Milky Lotion (1)

A milky lotion of the following composition was prepared.

| Component | (wt %) |
| --- | --- |
| Stearic acid | 2 |
| Cetanol | 1 |
| Octyldodecyl myristate | 5 |
| Liquid paraffin | 10 |
| Acrylic acid-alkyl methacrylate copolymer | 0.5 |
| Polyoxyethylene monostearate | 0.5 |
| Butyl parabene | 0.1 |
| 1,3-Butylene glycol | 5 |
| Carboxymethylcellulose | 0.1 |
| Sodium hydroxide | Appropriate amount |
| Methyl parabene | 0.1 |
| Fermented product* | 1 |
| Perfume | 0.05 |
| Purified water | Balance |

*Test product 21

Reference Example 4

Milky Lotion (2)

A milky lotion of the following composition was prepared.

| Component | (wt %) |
| --- | --- |
| Squalane | 10 |
| Jojoba oil | 2 |
| Beef tallow | 1 |
| Cholesteryl hydroxystearate | 0.1 |
| Batyl stearate | 1 |

-continued

| Component | (wt %) |
|---|---|
| Stearic acid | 1 |
| Luric acid | 1 |
| Hydrophobic glycerol monostearate | 2 |
| Polyethylene glycol monostearate | 2 |
| Methylpolysiloxane | 0.1 |
| Acetic acid-dl-α-tocopherol | 0.1 |
| Natural vitamin E | 0.001 |
| Stearyl glycyrrhetinate | 0.1 |
| Butyl parabene | 0.1 |
| Purified water | Balance |
| *Lactobacillus* culture broth | 10 |
| Fermented product* | 20 |
| EDTA-2Na | 0.1 |
| Potassium hydroxide | Appropriate amount |
| 1,3-Butylene glycol | 5 |
| Carageenan | 0.1 |
| Glycolic acid | 5 |
| Lactic acid | 3 |
| Glycerol | 3 |
| Methyl parabene | 0.1 |
| Sodium hyaluronate | 0.5 |
| Perfume | 0.05 |
| Mori cortex extract | 0.1 |
| Chlorohexidine gluconate | 0.01 |

*Test product 21

Reference Example 5

Moisturizing Cream (1)

A moisturizing cream of the following composition was prepared.

| Component | (wt %) |
|---|---|
| Stearic acid | 4 |
| Cetanol | 2 |
| Jojoba oil | 5 |
| Squalane | 10 |
| Polyoxyethylene sorbitan monostearate | 2 |
| Sorbitan monostearate | 3 |
| Butyl parabene | 0.1 |
| 1,2-Pentane diol | 2 |
| Sodium hydroxide | 0.05 |
| Fermented product* | 0.01 |
| Sodium hyaluronate | 0.1 |
| Perfume | 0.05 |
| Purified water | Balance |

*Test product 21

Reference Example 6

Moisturizing Cream (2)

A moisturizing cream of the following composition was prepared.

| Component | (wt %) |
|---|---|
| Squalane | 10 |
| Jojoba oil | 5 |
| Cetyl 2-ethylhexanoate | 5 |
| Cholesteryl hydroxystearate | 1 |
| Beef tallow | 1 |
| Bees wax | 1 |
| Batyl stearate | 2 |

-continued

| Component | (wt %) |
|---|---|
| Behenyl alcohol | 1 |
| Stearic acid | 0.3 |
| Behenic acid | 0.2 |
| Acrylic acid-alkyl methacrylate copolymer | 0.3 |
| Methylpolysiloxane | 0.1 |
| Acetic acid-dl-α-tocopherol | 0.1 |
| Natural vitamin E | 0.001 |
| Stearyl glycyrrhetinate | 0.1 |
| Polyoxyethylene monostearate | 0.5 |
| Purified water | Balance |
| *Lactobacillus* culture broth | 10 |
| Fermented product* | 15 |
| Sodium hydroxide | Appropriate amount |
| Glycerol | 10 |
| 1,2-Pentane diol | 5 |
| Carageenan | 0.1 |
| Sodium hyaluronate | 0.2 |
| Glycolic acid | 2 |
| Lactic acid | 1 |
| Perfume | 0.1 |
| Mori cortex extract | 0.1 |

*Test product 21

Reference Example 7

Essence

An essence of the following composition was prepared.

| Component | (wt %) |
|---|---|
| Pentylene glycol | 3 |
| *Lactobacillus* culture broth | 5 |
| Trimethyl glycine | 1 |
| Purified water | Balance |
| Carboxyvinyl polymer | 0.1 |
| Moutan cortex extract | 0.1 |
| Seaweed extract | 0.1 |
| Horse chestnut extract | 0.1 |
| Carageenan | 0.1 |
| Sodium hyaluronate | 0.1 |
| Glycerol | 5 |
| Squalane | 1 |
| Methylphenyl polysiloxane | 1 |
| Polymethacryloyloxyethyl phosphoryl choline solution | 2 |
| Behenyl alcohol | 0.1 |
| Polyoxyethylene sorbitan monostearate | 0.2 |
| Glycerol monostearate | 0.1 |
| Retinyl palmitate | 0.1 |
| Stearyl glycyrrhizinate | 0.1 |
| Fermented product* | 5 |
| Perfume | 0.1 |
| Sodium hydroxide | Appropriate amount |

*Test product 21

Reference Example 8

Cleansing Cream

A cleansing cream of the following composition was prepared.

| Component | (wt %) |
|---|---|
| Liquid paraffin | 40 |
| Octyldodecyl myristate | 10 |
| Isostearic acid | 1 |

-continued

| Component | (wt %) |
|---|---|
| Petroleum jelly | 10 |
| Jojoba oil | 1 |
| Behenyl alcohol | 1 |
| Bees wax | 2 |
| Stearic acid | 1 |
| Acrylic acid-alkyl methacrylate copolymer | 0.5 |
| Polyoxyethylene monostearate | 0.5 |
| Natural vitamin E | 0.001 |
| Butyl parabene | 0.1 |
| Stearyl glycyrrhetinate | 0.1 |
| Purified water | Balance |
| Fermented product* | 5 |
| 1,3-Butylene glycol | 5 |
| Methyl parabene | 0.1 |
| *Lactobacillus* culture broth | 10 |
| Sodium hyaluronate | 0.1 |
| Glycolic acid | 0.1 |
| Lactic acid | 0.1 |
| Perfume | 0.1 |
| Triethanolamine | Appropriate amount |
| Mori cortex extract | 0.1 |

*Test product 21

Reference Example 9

Washing Cream

A washing cream of the following composition was prepared.

| Component | (wt %) |
|---|---|
| Behenic acid | 1 |
| Luric acid | 5 |
| Myristic acid | 10 |
| Stearic acid | 5 |
| Palmitic acid | 5 |
| Glycerol | 20 |
| Purified water | Balance |
| Fermented product* | 1 |
| EDTA-2Na | 0.1 |
| Sodium benzoate | 0.1 |
| Potassium hydroxide | Appropriate amount |
| Diethanol amide luric acid | 0.1 |
| Polyethylene glycol distearate | 0.1 |
| Polyoxyethylene (20) coconut oil fatty acid sorbitan | 2 |
| Behenyl alcohol | 1 |
| Stearyl glycyrrhetinate | 0.1 |
| Natural vitamin E | 0.001 |
| Lactic acid | 1 |
| Glycolic acid | 1 |
| Sodium hyaluronate | 0.1 |
| *Lactobacillus* culture broth | 5 |
| Perfume | 0.1 |
| Mori cortex extract | 0.1 |

*Test product 21

Reference Example 10

Massage Cream

A massage cream of the following composition was prepared.

| Component | (wt %) |
|---|---|
| Liquid paraffin | 30 |
| Liquid isoparaffin | 5 |
| Octyldodecyl myristate | 1.0 |
| Petroleum jelly | 10 |
| Beef tallow | 1 |
| Cholesteryl hydroxystearate | 1 |
| Bees wax | 2 |
| Behenyl alcohol | 1 |
| Batyl alcohol | 1 |
| Hydrophobic glycol monostearate | 4 |
| Methylpolysiloxane | 0.1 |
| Acetic acid-dl-α-tocopherol | 0.1 |
| Natural vitamin E | 0.001 |
| Stearyl glycyrrhetinate | 0.1 |
| Butyl parabene | 0.1 |
| Polyoxyethylene sorbitan monostearate | 4 |
| Sodium hydroxide | Appropriate amount |
| Purified water | Balance |
| Fermented product* | 10 |
| *Lactobacillus* culture broth | 5 |
| Polyethylene glycol monostearate | 0.1 |
| Glycerol | 4 |
| Methyl parabene | 0.1 |
| 1,3-Butylene glycol | 5 |
| Sodium hyaluronate | 0.1 |
| Glycolic acid | 1 |
| Lactic acid | 1 |
| Perfume | 0.1 |
| Mori cortex extract | 0.1 |
| Chlorohexidine gluconate | 0.01 |

*Test product 21

Reference Example 11

Pack

A pack of the following composition was prepared.

| Component | (wt %) |
|---|---|
| *Lactobacillus* culture broth | 10 |
| Purified water | Balance |
| Fermented product* | 20 |
| dl-malic acid | 0.1 |
| Sodium hydroxide | Appropriate amount |
| Glycerol | 5 |
| Glycolic acid | 5 |
| Polyvinyl alcohol | 15 |
| Ethanol | 5 |
| Methyl parabene | 0.1 |
| Sodium hyaluronate | 0.5 |
| Polyoxyethylene polyoxypropylene glycol | 1 |
| Stearyl glycyrrhetinate | 0.1 |
| Acetic acid-dl-tocopherol | 0.1 |
| Natural vitamin E | 0.1 |
| Mori cortex extract | 0.1 |
| Chlorohexidine gluconate | 0.01 |
| Perfume | 0.1 |

*Test product 21

INDUSTRIAL APPLICABILITY

In the skin preparation for external use of the present invention, the effect of epidermic cell activation possessed by vitamin A and the derivatives thereof is synergistically promoted by a fermented product. At the same time, the effect of promoting hyaluronic acid production possessed by the vitamin A and derivatives thereof are supplemented by the same effect exhibited by the fermented product, resulting in the skin preparation excelling in a roughness preventing and improving effect, a cornification improving effect, a moisturizing effect, and an effect of preventing and improving wrinkled or loosened skin. The skin preparation is effective in preventing skin aging as a skin preparation for external application such as a cosmetic composition and a quasi-drug composition.

The skin preparation for external application of the present invention can also be used as a medicine, for example, as an ache suppressor or improver for diseases induced by a decrease in the amount of hyaluronic acid in tissues such as rheumatoid arthritis and traumatic arthritis, a curing agent for promoting growth of granulation tissues in the initial stage of thermal burn treatment, an acne treatment drug, a psoriasis treating agent, a wrinkle treating agent, and an optically aged skin treating agent.

The invention claimed is:

1. A composition comprising:
   at least one form of vitamin A, and
   a fermented extract that is obtained by:
   culturing a microorganism belonging to the genus *Bifidobacterium* in a medium obtained by extraction of soybeans to form a fermented culture medium,
   mixing the fermented culture medium with a lower alcohol having 1 to 5 carbon atoms or a polyhydric alcohol and
   recovering a fermented extract by removing some or all of the solid components in the fermented culture medium, and optionally,
   deodorizing said fermented extract.

2. The composition of claim 1, wherein the vitamin A is at least one of all-trans-retinoic acid (RA), all-trans-retinol (ROH), or retinyl palmitate.

3. The composition of claim 1, wherein said medium comprises soybean milk.

4. The composition of claim 1, wherein said fermented extract is produced by culturing said microorganism in said medium under a nitrogen atmosphere.

5. The composition of claim 1, wherein said alcohol mixed with the fermented culture medium is ethanol.

6. The composition of claim 1, wherein the fermented culture medium is mixed with a polyhydric alcohol.

7. The composition of claim 1, which is deodorized, optionally under a nitrogen atmosphere, after mixing with the alcohol.

8. The composition of claim 1, wherein the fermented extract is deodorized by contacting it with talc.

9. The composition of claim 1, wherein the fermented extract is deodorized by contacting it with at least one carbonate.

10. The composition of claim 1, wherein the fermented extract is deodorized by contacting it with magnesium carbonate or calcium carbonate, or both.

11. The composition of claim 1, wherein said fermented extract is deodorized by stirring at a temperature of 20° C. or less.

12. The composition of claim 1, wherein said fermented extract is pH adjusted by the addition of an organic acid.

13. The composition of claim 1, wherein said fermented extract and vitamin A are present in an amount which promotes hyaluronic acid synthesis or increases epidermal cell metabolic activity, or both.

14. A cosmetic comprising the composition of claim 1.

15. The cosmetic of claim 14, which contains 0.5 to 10% of said fermented extract and which has a pH ranging 3.5–5.0.

16. A method for making a deodorized soybean extract containing at least one form of vitamin A comprising:
   culturing a lactic acid producing microorganism belonging to the genus *Bifidobacterium* in a medium comprising a soybean extract to form a fermented culture medium,
   mixing the fermented culture medium with a lower alcohol having 1 to 5 carbons,
   recovering a fermented extract by removing some or all of the solid components in the fermented culture medium,
   deodorizing said fermented culture medium with at least one carbonate and/or with talc to form a deodorized composition suitable for external application to the skin,
   and adding at least one form of vitamin A to said extract.

17. A deodorized soybean extract prepared by the method of claim 16.

18. The deodorized soybean extract of claim 17 that has a reduced odor compared to a similar soybean extract which has not been deodorized with at least one carbonate and/or talc.

19. A composition comprising:
   at least one form of Vitamin A, and
   the deodorized soybean extract of claim 17.

* * * * *

UNITED STATES PATENT AND TRADEMARK OFFICE
CERTIFICATE OF CORRECTION

PATENT NO. : 7,090,875 B2  Page 1 of 1
APPLICATION NO. : 10/450453
DATED : August 15, 2006
INVENTOR(S) : Miyazaki et al.

It is certified that error appears in the above-identified patent and that said Letters Patent is hereby corrected as shown below:

On the title page, Item (75), the Inventors are incorrect. Item (75) should read:

--(75) Inventors: Kouji Miyazaki, Tokyo (JP); Satoshi Yoshikawa, Tokyo (JP); Ryoko Iizuka, Tokyo (JP); Takashi Kinoshita, Tokyo (JP); Naohito Saito, Tokyo (JP); Katsuyoshi Chiba, Tokyo (JP); Naomi Kondo, Tokyo (JP); Tomoko Hanamizu, Tokyo (JP) --

Signed and Sealed this

Sixth Day of February, 2007

JON W. DUDAS
*Director of the United States Patent and Trademark Office*